United States Patent
Yan

(10) Patent No.: US 12,351,828 B2
(45) Date of Patent: Jul. 8, 2025

(54) METHOD FOR CONSTRUCTING HEPATIC PROGENITOR CELL-LIKE CELL BANK, CELL LINES PREPARED THEREFROM AND APPLICATION THEREOF

(71) Applicants: SHANGHAI CELLIVER BIOTECHNOLOGY CO., LTD., Shanghai (CN); SHANGHAI CRYOWISE MEDICAL TECHNOLOGY CO., LTD., Shanghai (CN)

(72) Inventor: Hexin Yan, Shanghai (CN)

(73) Assignees: SHANGHAI CELLIVER BIOTECHNOLOGY CO., LTD., Shanghai (CN); SHANGHAI CRYOWISE MEDICAL TECHNOLOGY CO., LTD., Shanghai (CN)

( * ) Notice: Subject to any disclaimer, the term of this patent is extended or adjusted under 35 U.S.C. 154(b) by 807 days.

(21) Appl. No.: 17/622,838

(22) PCT Filed: Apr. 24, 2020

(86) PCT No.: PCT/CN2020/086659
§ 371 (c)(1),
(2) Date: Dec. 26, 2021

(87) PCT Pub. No.: WO2021/004129
PCT Pub. Date: Jan. 14, 2021

(65) Prior Publication Data
US 2022/0411758 A1  Dec. 29, 2022

(30) Foreign Application Priority Data
Jul. 11, 2019 (CN) .......... 201910623436.9

(51) Int. Cl.
| | | |
|---|---|---|
| *C12N 5/071* | (2010.01) | |
| *A61K 35/407* | (2015.01) | |
| *A61P 1/16* | (2006.01) | |
| *C12N 15/86* | (2006.01) | |
| *G01N 33/50* | (2006.01) | |

(52) U.S. Cl.
CPC .......... *C12N 5/0672* (2013.01); *A61K 35/407* (2013.01); *A61P 1/16* (2018.01); *C12N 5/0671* (2013.01); *C12N 15/86* (2013.01); *G01N 33/5014* (2013.01); *G01N 33/5067* (2013.01); *C12N 2503/02* (2013.01); *C12N 2510/04* (2013.01); *C12N 2513/00* (2013.01); *C12N 2740/15043* (2013.01)

(58) Field of Classification Search
None
See application file for complete search history.

(56) References Cited

FOREIGN PATENT DOCUMENTS

| CN | 101228266 A | 7/2008 |
| CN | 108300688 A | 7/2018 |
| CN | 108330099 A | 7/2018 |

OTHER PUBLICATIONS

Burkard et al. Generation of proliferating human hepatocytes using Upcyte® technology: characterisation and applications in induction and cytotoxicity assays. Xenobiotica. Oct. 2012;42(10):939-56. doi: 10.3109/00498254.2012.675093. Epub Apr. 24, 2012. PMID: 22524704. (Year: 2012).*
Wu et al. Reversible transition between hepatocytes and liver progenitors for in vitro hepatocyte expansion. Cell Res. May 2017;27(5):709-712. doi: 10.1038/cr.2017.47. Epub Apr. 4, 2017. PMID: 28374751; PMCID: PMC5520858. (Year: 2017).*
Aznan AN, Abdul Karim N, Wan Ngah WZ, Jubri Z. Critical factors for lentivirus-mediated PRDX4 gene transfer in the HepG2 cell line. Oncol Lett. Jul. 2018;16(1):73-82. doi: 10.3892/ol.2018.8650. Epub May 7, 2018. PMID: 29930713; PMCID: PMC6006497. (Year: 2018).*
Godoy et al., Gene network activity in cultivated primary hepatocytes is highly similar to diseased mammalian liver tissue. Arch Toxicol. Oct. 2016;90(10):2513-29. doi: 10.1007/s00204-016-1761-4. Epub Jun. 23, 2016. PMID: 27339419; PMCID: PMC5043005. (Year: 2016).*
Tomiya T, et al. The mitogenic activity of hepatocyte growth factor on rat hepatocytes is dependent upon endogenous transforming growth factor-alpha. Am J Pathol. Nov. 2000;157(5):1693-701. doi: 10.1016/s0002-9440(10)64806-7. PMID: 11073828; PMCID: PMC1885723. (Year: 2000).*
Neuhuber B, Swanger SA, Howard L, Mackay A, Fischer I. Effects of plating density and culture time on bone marrow stromal cell characteristics. Exp Hematol. Sep. 2008;36(9):1176-85. doi: 10.1016/j.exphem.2008.03.019. Epub May 20, 2008. PMID: 18495329; PMCID: PMC2603339. (Year: 2008).*

(Continued)

*Primary Examiner* — Evelyn Y Pyla
*Assistant Examiner* — Jagamya Vijayaraghavan

(57) ABSTRACT

The invention provides a method for constructing a hepatic progenitor cell-like cell bank, including successively performing following processes to human primary hepatocyte cultures from different donor sources: transformation-culture, cryopreservation treatment, proliferation-culture, a first subculture treatment, virus infection, a second subculture treatment, continuous selection-culture and continuous subculture. In the method for constructing a heterogenous immortal hepatic progenitor cell-like cell bank of the present invention, the human primary hepatocyte culture of each of the donor sources is transformation-cultured before the proliferation-culture, which is beneficial in endowing the human primary hepatocyte cultures with good proliferation performance. Once combined with subsequent controlling of culture parameter, the immortal hepatic progenitor cell-like cell lines obtained from different donor sources may have good in vitro proliferation ability. The invention also provides an application of the hepatic progenitor cell-like cell bank and cell lines obtained by the construction method.

3 Claims, 10 Drawing Sheets

(56) References Cited

OTHER PUBLICATIONS

Spieker-Polet H, Polet H. Identification of albumin as the serum factor essential for the growth of activated human lymphocytes. J Biol Chem. Feb. 25, 1976;251(4):987-92. PMID: 2610. (Year: 1976).*
Tsuruga et al. Cell Transplant. 2008, pp. 1083-1094 (Year: 2008).*
Wu Supplementary, Reversible transition between hepatocytes and liver progenitors for in vitro hepatocyte expansion. Cell Res. May 2017;27(5):709-712. 2017, 7 pages (Year: 2017).*
Gong-Bo Fu et al., Expansion and Differentiation of Human Hepatocyte-derived Liver Progenitor-like Cells and Their Use for the Study of Hepatotropic Pathogens, Cell Research, Oct. 25, 2018, pp. 1-15.
Hualian Hang et el., Establishment and Biological Study of Immortalized Human Hepatocyte Cell Line, Jiangsu Medical Journal, Nov. 2011, pp. 2624-2627, vol. 37, No. 22, China Academic Journal Electronic Publishing House.
International Search Report of PCT Patent Application No. PCT/CN2020/086659 issued on Jul. 22, 2020.

* cited by examiner

METHOD FOR CONSTRUCTING HEPATIC PROGENITOR CELL-LIKE CELL BANK, CELL LINES PREPARED THEREFROM AND APPLICATION THEREOF

BACKGROUND OF THE INVENTION

1. Field of the Invention

The present invention relates to the field of biotechnology, in particular to a method for constructing hepatic progenitor cell-like cell bank, cell lines prepared therefrom and applications thereof.

2. Description of the Related Art

Hepatic failure is the end-stage manifestation of severe liver disease, and the mortality rate of patients can be as high as 50%~90%. Wherein, the problem of drug-induced hepatic injury caused by adverse drug reactions in patients is more prominent, which accounts for more than 50% of acute hepatic failure cases, so that drug developments are failed or withdrawn after marketing.

Most of the reasons for drug development failure or withdrawal after marketing are due to specific toxicity to patients. In the prior arts, the immortalization of hepatocytes is one of the important ways to solve the source of hepatocytes. Usually, primary hepatocytes or hepatocyte-like cells derived from induced stem cells are immortalized. Then, the obtained cell lines are applied to hepatic metabolic heterogeneity studies to find solutions to drug-specific toxicity problems.

The China invention patent application with publication number of CN108330099A discloses a method for culturing and expanding individualized hepatocytes. The method puts genetically modified liver parenchymal cells into a hepatocyte proliferation medium for culture and proliferation, and then the obtained hepatocytes were differentiated and cultured to obtain mature hepatocytes. However, since the method genetically modifies the hepatocytes first then follows by proliferation-culture and differentiation-culture, which easily affects the in vitro proliferation ability of the obtained mature hepatocytes. However, the donor source is single, which makes it impossible to carry out idiosyncratic drug-specific toxicity studies.

Therefore, it is necessary to develop a novel method for constructing hepatic progenitor cell-like cell bank and application thereof to avoid the above-mentioned problems in the prior art.

SUMMARY OF THE INVENTION

The purpose of the present invention is providing a method for constructing a hepatic progenitor cell-like cell bank, cell lines prepared therefrom and applications thereof, so as to obtain immortal hepatic progenitor cell-like cell lines with good in vitro proliferation ability, and facilitating the study of drug-specific toxicity.

To achieve the above objectives, a method for constructing a hepatic progenitor cell-like cell bank of the present invention includes the steps of:

S1: Providing human primary hepatocyte cultures from different donor sources, transformation-culturing a human primary hepatocyte culture of each of the donor sources at a seeding density of $0.5 \times 10^4$-$5 \times 10^4$ cells/cm$^2$ for 7-14 days, and performing cryopreservation treatment to the hepatic progenitor cell-like cell line of each of the donor sources obtained after the transformation-culture to obtain a heterogeneous hepatic progenitor cell-like cell bank;

S2: Thawing and proliferation-culturing the hepatic progenitor cell-like cell line of each of the donor sources to obtain adherent cells of the different donor sources respectively, wherein the confluence rate of the adherent cells of each of the donor sources is 70%-90%;

S3: Performing a first subculture treatment and virus infection successively to the adherent cells of each of the donor sources, and replacing a medium during the virus infection;

S4: Performing a second subculture treatment with a passage number of 2 or 3 to the culture of each of the donor sources obtained after the virus infection, and continuously selection-culturing the culture obtained after the second subculture treatment by a selecting medium to obtain infected cultures of the different donor sources;

S5: Continuously-subculturing the infected culture of each of the donor sources with a passage ratio of 1:2-1:4 and a passage number of 5-10 to obtain the hepatic progenitor cell-like cell bank.

The beneficial effect of the method for constructing a heterogenous immortal hepatic progenitor cell-like cell bank of the present invention is: in the step S11, the human primary hepatocyte culture of each of the donor sources is transformation-cultured at a seeding density of $0.5 \times 10^4$-$5 \times 10^4$ cells/cm$^2$ for 7-14 days, which is beneficial in endowing the human primary hepatocyte cultures with good proliferation performance. Once combined with subsequent controlling of the second subculture treatment, the continuous selection-culture and the continuous-subculture, the immortal hepatic progenitor cell-like cell lines obtained from different donor sources may have good in vitro proliferation ability and are conducive to the development of drug-specific toxicity studies.

Preferably, in the step S1, after the transformation-culture is completed, the culture obtained after transformation-cultured is proliferation-cultured successively for 2 or 3 times and is thereby performed with the cryopreservation treatment. The beneficial effect is that it further endows the human primary hepatocyte culture with good proliferation performance.

Preferably, in the step S2, the hepatic progenitor cell-like cell line is proliferation-cultured at a seeding density of $0.5 \times 10^4$-$5 \times 10^4$ cells/cm$^2$, and the medium is replaced every day within three days after starting the proliferation-culture. The beneficial effect is that the adherent cells can be obtained as soon as possible while ensuring cell viability.

Preferably, in the step S3, the adherent cells of each of the donor sources are performed with the first subculture treatment at a seeding density of $2 \times 10^4$-$4 \times 10^4$ cells/cm$^2$ for 24 hours. The beneficial effect is that the proper seeding density is beneficial to the effective subsequent virus infection.

Preferably, in the step S3, the culture obtained after the first subculture treatment is performed with virus infection at a seeding density of $2 \times 10^4$-$4 \times 10^4$ cells/cm$^2$. The beneficial effect is that the proper seeding density is beneficial to the effective virus infection.

More preferably, a medium of the culture obtained after the first subculture treatment is replaced at 6-12 hours after adding a DMEM/12 medium, lentivirus and a polybrene suspension, and then the culture is continuously cultured for 24-72 hours to complete the virus infection, wherein a ratio of the number of the lentivirus to the adherent cells is 0.5-60.

Preferably, in the step S4, the culture of each of the donor sources obtained after the virus infection is performed with a second subculture treatment at a seeding density of $2 \times 10^4$-

$4\times10^4$ cells/cm$^2$ for 5-7 days; and the medium is replaced every 2-3 days during the second subculture treatment.

Preferably, the selecting medium is a TEM medium.

Preferably, in the step S5, the infected culture of each of the donor sources is performed with continuous-subculture at a seeding density of $2\times10^4$-$4\times10^4$ cells/cm$^2$ for 24 hours.

Since the immortal hepatic progenitor cell-like cell lines in the heterogeneous immortal hepatic progenitor cell-like cell bank prepared by the construction method have good in vitro proliferation ability, it is conducive to the studies on the specific toxicity of a drug by constructing an in vitro three-dimensional hepatocyte model by the heterogeneous immortal hepatic progenitor cell-like cell bank and testing the specific hepatotoxicity of the drug by using the in vitro three-dimensional hepatocyte model. In addition, the immortal hepatic progenitor cell-like cell lines prepared by the construction method can be applied to bioartificial liver and hepatic cell transplantation.

The present invention also provides an immortal hepatic progenitor cell-like cell line having a category name of 81.5 prepared by using the construction method, and the immortal hepatic progenitor cell-like cell line is preserved in China Center for Type Culture Collection in Wuhan University, Wuhan, China. The preservation number is CCTCC NO: C2019125.

Specifically, the culture is received by the China Center for Type Culture Collection on Jun. 11, 2019 and is named as immortal human hepatic progenitor cell-like cell line ALI-CELL-81.5. The culture is tested and identified as alive on Jun. 24, 2019. The immortal human hepatic progenitor cell-like cell line ALI-CELL-81.5 is the immortal hepatic progenitor cell-like cell line having a category name of 81.5 according to the present invention.

The China Center for Type Culture Collection shall, upon request, store the culture for 30 years starting from Jun. 11, 2019, and shall continue to store it for another 5 years after receiving the request to provide culture samples before the expiration date.

The present invention further provides an application of the immortal hepatic progenitor cell-like cell line in bioartificial liver and hepatic cell transplantation, wherein the hepatocytes proliferated from the immortal hepatic progenitor cell-like cell line secretes an exogenous human growth factor during being applied in a bioartificial liver treatment.

Preferably, the at least one exogenous human growth factor includes any one or more of a human hepatocyte growth factor, a human transforming growth factor-α and a human interleukin-6.

DESCRIPTION OF THE PREFERRED EMBODIMENTS

Figure 1:
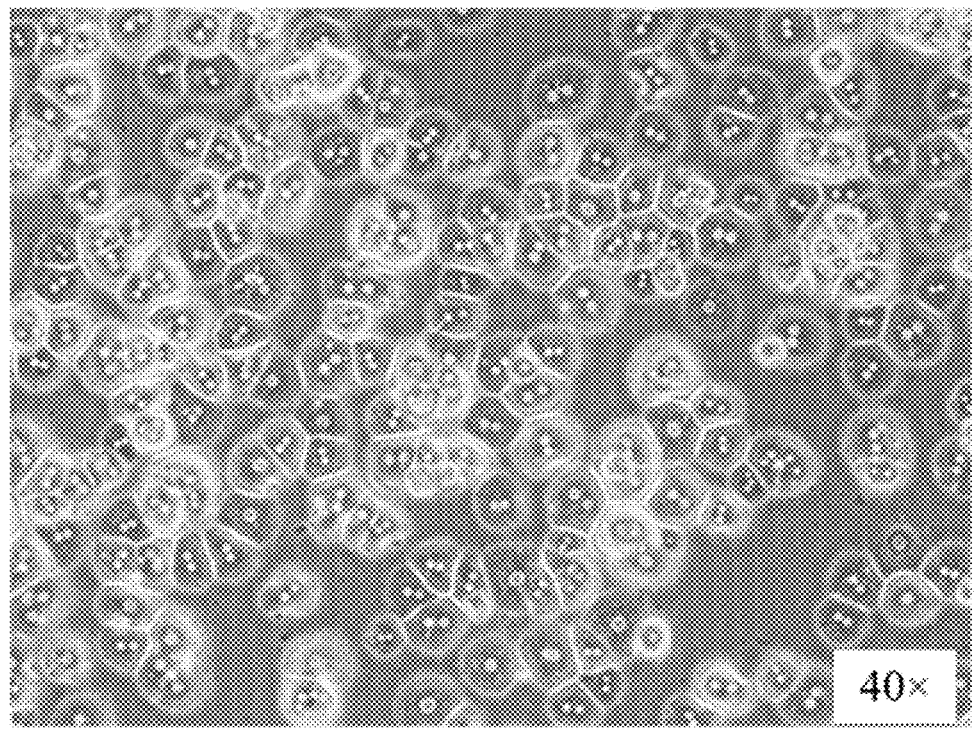
FIG. 1 is a schematic diagram of the morphology of the human primary hepatocytes of the present invention.

To make the objectives, technical solutions and advantages of the present invention clearer, the technical solutions in the embodiments of the present invention will be described clearly and completely with reference to the accompanying drawings of the present invention. Obviously, the described embodiments are part of, but not all of, the embodiments of the present invention. Based on the embodiments of the present invention, all other embodiments obtained by those skilled in the art without creative work shall fall within the protection scope of the present invention. Unless otherwise defined, the technical or scientific terms used herein shall have the usual meanings understood by those skilled in the art related to the present invention. As used herein, "comprising" and other similar terms mean that the elements or objects appearing before the term encompass the elements or objects listed after the term and their equivalents, without excluding other elements or objects.

The main sources of the reagents in the embodiments are as follows:

The TEM culture medium is from Shanghai Celliver Biotechnology Co., Ltd.; Matrigel is produced by Corning Incorporated, the catalog number is 356234; the polybrene suspension is produced by Shanghai Yeasen Biotech Co., Ltd., the catalog number is 40804ES76; Trypsin solution, DMEM/12 medium and HepX medium are produced by Shanghai Basal Media Technologies Co., Ltd., the product numbers are S310KJ, L110KJ and X071A1, respectively.

The main sources of the instruments in the embodiments are as follows:

The cell culture plates with different numbers of holes and the culture dishes with different diameters were all produced by NEST Science Co. Ltd.; the cell culture incubator was purchased from ESCO Singapore, the product model is CLL-170B-8; the cell inverted microscope was purchased from Nikon Co., Ltd., the product model is Ta2-FL.

In view of the problems in the prior art, the embodiment of the present invention provides a method for constructing a hepatic progenitor cell-like cell bank, including:

S1: Providing human primary hepatocyte cultures from different donor sources, transformation-culturing a human primary hepatocyte culture of each of the donor sources at a seeding density of $0.5\times10^4$-$5\times10^4$ cells/cm$^2$ for 7-14 days, and performing cryopreservation treatment to the hepatic progenitor cell-like cell line of each of the donor sources obtained after the transformation-culture to obtain a heterogeneous hepatic progenitor cell-like cell bank;

S2: Thawing and proliferation-culturing the hepatic progenitor cell-like cell line of each of the donor sources to obtain adherent cells of the different donor sources respectively, wherein the confluence rate of the adherent cells of each of the donor sources is 70%-90%;

S3: Performing the first subculture treatment and virus infection successively to the adherent cells of each of the donor sources, and replacing a medium during the virus infection;

S4: Performing the second subculture treatment with a passage number of 2 or 3 to the culture of each of the donor sources obtained after the virus infection, and continuously selection-culturing the culture obtained after the second subculture treatment by a selecting medium to obtain infected cultures of the different donor sources;

S4: Continuously-subculturing the infected culture of each of the donor sources with a passage ratio of 1:2-1:4 and a passage number of 5-10 to obtain the hepatic progenitor cell-like cell bank.

The hepatic progenitor cell-like cell bank in the embodiment of the present invention is a heterogeneous immortal hepatic progenitor cell-like cell bank.

In some embodiments of the present invention, the cryopreservation treatment is performed by using cell freezing medium and liquid nitrogen.

In some embodiments of the present invention, the virus used for the virus infection is stated in the China invention patent application with publication number of CN108330099A. Specifically, it expresses the SV40 virus large T antigen gene, HPV virus E6E7 gene or ubiquitin ligase gene.

In some embodiments of the present invention, the selection medium is a TEM medium.

In the step S1 of some embodiments of the present invention, the culture obtained after the transformation-cultured successively for 2-3 times is proliferation-cultured and performed with the cryopreservation treatment after transformation-cultured.

In the step S2 of some embodiments of the present invention, the hepatic progenitor cell-like cell line is proliferation-cultured at a seeding density of $0.5\times10^4$-$5\times10^4$ cells/cm$^2$, and the medium is replaced every day within three days after starting proliferation-culture.

In the embodiments of the present invention, the immortal hepatic progenitor cell-like cell lines prepared by the construction method can be applied to bioartificial liver, hepatic cell transplantation, and testing of the specific hepatotoxicity of drugs.

Hereinafter, the details will be described by Embodiments 1-7, wherein described different donor sources are all obtained from discarded surgical specimens from Shanghai Eastern Hepatobiliary Surgery Hospital. The patient's consent was obtained before the operation and the informed consent was signed.

Embodiment 1

The present embodiment provides a first hepatic progenitor cell-like cell line having a category name of 81.5 which is preserved in the China Center for Type Culture Collection, the first immortal hepatic progenitor cell-like cell line with the preservation number of CCTCC NO: C2019125, and a method for constructing an immortal hepatic progenitor cell-like cell line.

The coating solution in the present embodiment is a mixed solution of HepX medium and Matrigel, and the volume ratio of the HepX medium to the Matrigel is 80:1.

When the incubator is a 6-well cell culture plate, 250-350 microliters of the coating solution is added into each culture well to perform a coating treatment in advance.

When the incubator is a 12-well cell culture plate, 150-200 microliters of the coating solution is added into each culture well to perform the coating treatment in advance.

When the incubator is a cell culture dish with a diameter of 6 cm, 500-700 microliters of the coating solution is added for the coating treatment.

When the incubator is a cell culture dish with a diameter of 10 cm, 1000-1500 microliters of the coating solution is added for the coating treatment.

When the incubator is a cell culture dish with a diameter of 15 cm, 2000-3000 microliters of the coating solution is added for the coating treatment.

The period of the coating treatment is 30-120 minutes.

The cell culture incubator involved in the present embodiment is configured to provide a constant internal temperature of 37° C., saturated humidity, and a carbon dioxide concentration of 5%. Except for the process carried out in the cell culture incubator, other operations are carried out in a laminar flow bench under room temperature.

In the present embodiment, the specific implementation of digesting the culture with a cell digestion solution is a conventional technical means known by those skilled in the art, and will not be repeated here. The cell digestion agent is trypsin digestion solution.

The method for constructing the first immortal hepatic progenitor cell like cell-line is specifically:

In the step S1, human primary hepatocyte cultures are provided from different donor sources; a human primary hepatocyte culture of each of the donor sources is transformation-cultured at a seeding density of $1\times10^4$ cells/cm$^2$ for 7 days; and the first hepatic progenitor cell-like cell line obtained after transformation-cultured is proliferation-cultured for 3 times successively.

Specifically, any one of the two-step perfusion method or the chopping digestion method is used to separate the tissue adjacent to the human hepatic hemangioma derived from the first donor source to obtain a first human primary hepatocyte culture. The specific implementation of the two-step perfusion method is stated in the "Expansion and Differentiation of Human Hepatocyte-derived Liver Progenitor-like Cells and Their Use for the Study of Hepatotropic Pathogens" published in Issue 1, Volume 29, 2018, Cell Research. The specific implementation of the chopping digestion method is stated in the China invention patent application with the publication number CN108300688A. Both will not be repeated here.

After the first human primary hepatocyte culture is resuspended with TEM medium, the obtained resuspension mixture is seeded in the first cell culture plate at a seeding density of $1\times10^4$ cells/cm$^2$ in order to perform transformation-culture in a cell culture incubator to obtain the first hepatic progenitor cell-like cell line. The first cell culture plate is a 6-well cell culture plate, and each culture well is coated with a coating solution in advance.

The culture in the first cell culture plate is digested with trypsin digestion solution and then transferred to a culture dish with a diameter of 6 cm after transformation-cultured and is proliferation-cultured for the first time in a cell culture incubator for 7 days. The culture covering the bottom of the culture dish with a diameter of 6 cm is digested with trypsin digestion solution, then is transferred to a culture dish with a diameter of 10 cm, and is proliferation-cultured for the second time in the cell culture incubator for 4 days. The culture covering the bottom of the culture dish with a diameter of 10 cm is digested with the trypsin digestion solution, then is finally transferred to a culture dish with a diameter of 15 cm, and is proliferation-cultured for the third time in the cell culture incubator for 4 days. The culture covering the bottom of the culture dish obtained after the third time of proliferation-culture is digested with the trypsin digestion solution, and then is performed with cryopreservation treatment to obtain a cryopreservation culture to be proliferated.

In some embodiments of the present invention, the period of the transformation-culture is 7-14 days.

In the step S2, the cryopreservation culture to be proliferated is seeded, after thawed, on the second cell culture plate at a seeding density of $0.8\times10^4$ cells/cm$^2$ in the cell culture incubator for 4 days of proliferation-culture, thereby obtaining 80% of confluence rate of obtained adherent cells.

In some embodiments of the present invention, the confluence rate of the adherent cells is 70%-90%.

Specifically, the second cell culture plate is a 6-well cell culture plate and is coated with a coating solution in advance. Three days before starting of the proliferation-culture, the liquid in the second cell culture plate is replaced with new TEM medium every day to achieve stable proliferation.

In the step S3, after digesting the culture obtained by the proliferation-culture with the trypsin digestion solution, the obtained digested culture is seeded on the third cell culture plate at a seeding density of $3\times10^4$ cells/cm' to carry out the first subculture treatment in the cell culture incubator for 24 hours. After the first subculture treatment is completed, the supernatant in the third cell culture plate is removed, and then DMEM/12 medium, lentivirus suspension and virus infection enhancement suspension are added into the third cell culture plate, and the infection process is carried out in the cell culture incubator for 8 hours. After the infection process is completed, the liquid in the third cell culture plate is replaced with new DMEM/12 medium, and the culture is then cultured in the cell culture incubator for 48 hours to complete the virus infection.

Specifically, the third cell culture plate is a 6-well cell culture plate, the lentivirus in the lentivirus suspension is a lentivirus expressing the HPV E6E7 gene, and the virus infection enhancing suspension is a polybrene suspension. The ratio of the number of lentivirus in the lentivirus suspension to the adherent cells in the third cell culture plate is 20, 1 mL of DMEM/12 medium, 50 microliters of lentivirus and 10 microliters of the polybrene suspension are added to each culture well of the third cell culture plate, the concentration of the polybrene suspension is 8 mg/mL.

In some embodiments of the present invention, the ratio of the number of the lentivirus to the adherent cells in the third cell culture plate is 10-60. Specifically, the ratio of the number of the lentivirus to the number of adherent cells in the third cell culture plate is any one of 30, 40 or 50.

In some embodiments of the present invention, the period of infection process is 6-12 hours, specifically any one of 7, 9, 10, or 11. After the infection process is completed, the time for continuing the culture in the cell culture incubator is 24-72 hours, specifically 36 or 60 hours.

In the step S4, after digesting the culture obtained after the virus infection with the trypsin digestion solution, the obtained digested culture is seeded on the fourth cell culture plate at a seeding density of $3\times10^4$ cells/cm$^2$ to carry out the second subculture treatment with DMEM/12 medium in a cell culture incubator for 7 days with a passage number of 2.

Specifically, the fourth cell culture plate is a 12-well cell culture plate and is coated with a coating solution in advance.

During the second subculture treatment, the liquid in the fourth cell culture plate is replaced with new DMEM/12 medium every 2 days.

In some embodiments of the present invention, the passage number of the second subculture is 3. During the second subculture, the liquid in the fourth cell culture plate is replaced with new DMEM/12 medium every 3 days.

In the step S4, after the second subculture treatment is completed, the TEM medium is added to the fourth cell culture plate for the continuous-selection culture, and the resulting culture is seeded on the fifth cell culture plate at a seeding density of $3\times10^4$ cells/cm$^2$ after the cells reach 80-90% confluence. The continuous selection-culture is carried out in the cell incubator with a passage ratio of 1:3 and a passage number of 10. Thus, the first immortal hepatic progenitor cell-like cell line having a category name of 81.5 is obtained and preserved in the China Center for Type Culture Collection with the preservation number of CCTCC NO: C2019125.

Specifically, the fifth cell culture plate is a 6-well cell culture plate and is coated with a coating solution in advance.

The process of the continuous-subculture is specifically as follows: observing that the cell culture to be subcultured grows to 80-90% of the bottom of the culture wells, dividing the cell culture to be subcultured into 3 parts, and respectively substituting them into other three cell culture plates having the same structure as the fourth cell culture plate. Further, 2 mL of TEM medium is added to each culture well.

In some embodiments of the present invention, the passage ratio of the continuous-subculture is 1:2-1:4, and the passage number is 5-10.

Embodiment 2

The present embodiment provides a method for constructing a second immortal hepatic progenitor cell-like cell line and a second hepatic progenitor cell-like cell line obtained by the method for constructing the second immortal hepatic progenitor cell-like cell line.

The difference between the method for constructing the second immortal hepatic progenitor cell-like cell line and the method for constructing the first immortal hepatic progenitor cell-like cell line of Embodiment 1 is:

In the step S1, after the tissue adjacent to the human hepatic hemangioma obtained from the second donor source is separated, the obtained second human primary hepatocyte culture is transformation-cultured for 14 days to obtain the second hepatic progenitor cell-like cell line. The seeding density of the second human primary hepatocyte culture is $5 \times 10^4$ cells/cm$^2$. The subculture number of the proliferation-culture is 2, specifically the first proliferation-culture and the second proliferation-culture.

Embodiment 3

The present embodiment provides a method for constructing a third immortal hepatic progenitor cell-like cell line and a third hepatic progenitor cell-like cell line obtained by the method for constructing the third immortal hepatic progenitor cell-like cell line.

The difference between the method for constructing the third immortal hepatic progenitor cell-like cell line and the method for constructing the first immortal hepatic progenitor cell-like cell line of Embodiment 1 is:

In the step S1, after the tissue adjacent to the human hepatic hemangioma obtained from the third donor source is separated, the obtained third human primary hepatocyte culture is transformation-cultured as said to obtain the third hepatic progenitor cell-like cell line.

In the step S2, the cryopreservation culture to be proliferated is seeded, after thawed, on the second cell culture plate at a seeding density of $0.5 \times 10^4$ cells/cm$^2$.

Embodiment 4

The present embodiment provides a method for constructing a fourth immortal hepatic progenitor cell-like cell line and a fourth hepatic progenitor cell-like cell line obtained by the method for constructing the fourth immortal hepatic progenitor cell-like cell line.

The difference between the method for constructing the fourth immortal hepatic progenitor cell-like cell line and the method for constructing the first immortal hepatic progenitor cell-like cell line of Embodiment 1 is:

In the step S1, after the tissue adjacent to the human hepatic hemangioma obtained from the fourth donor source is separated, the obtained fourth human primary hepatocyte culture is transformation-cultured for 10 days to obtain the fourth hepatic progenitor cell-like cell line.

In the step S3, the seeding density of the digested culture seeded on the third cell culture plate is $2 \times 10^4$ cells/cm$^2$. The period of the infection process is 12 hours, and after the infection process is completed, the culture is continued for 72 hours to complete the virus infection.

In the step S4, the seeding density of the digested culture seeded on the fourth cell culture plate is $2 \times 10^4$ cells/cm$^2$.

In the step S5, the seeding density of the digested culture seeded on the fifth cell culture plate is $2 \times 10^4$ cells/cm$^2$, the passage ratio of the continuous-subculture is 1:2, and the passage number is 5.

Embodiment 5

The present embodiment provides a method for constructing a fifth immortal hepatic progenitor cell-like cell line and a fifth hepatic progenitor cell-like cell line obtained by the method for constructing the fifth immortal hepatic progenitor cell-like cell line.

The difference between the method for constructing the fifth immortal hepatic progenitor cell-like cell line and the method for constructing the first immortal hepatic progenitor cell-like cell line of Embodiment 1 is:

In the step S1, after the tissue adjacent to the human hepatic hemangioma obtained from the fifth donor source is separated, the obtained fifth human primary hepatocyte culture is transformation-cultured as described.

In the step S4, the seeding density of the digested culture seeded on the fourth cell culture plate is $4 \times 10^4$ cells/cm$^2$.

In the step S5, the seeding density of the digested culture seeded on the fifth cell culture plate is $4 \times 10^4$ cells/cm$^2$, the passage ratio of the continuous-subculture is 1:4, and the passage number is 8.

Embodiment 6

The present embodiment provides a method for constructing a sixth immortal hepatic progenitor cell-like cell line and a sixth hepatic progenitor cell-like cell line obtained by the method for constructing the sixth immortal hepatic progenitor cell-like cell line.

The difference between the method for constructing the sixth immortal hepatic progenitor cell-like cell line and the method for constructing the first immortal hepatic progenitor cell-like cell line of Embodiment 1 is:

In the step S1, after the tissue adjacent to the human hepatic hemangioma obtained from the sixth donor source is separated, the obtained sixth human primary hepatocyte culture is transformation-cultured as described.

Embodiment 7

The present embodiment provides a heterogeneous hepatic progenitor cell-like cell bank, a hepatic progenitor cell-like cell bank, and an in vitro three-dimensional hepatocyte model. The hepatic progenitor cell-like cell bank is a heterogeneous immortal hepatic progenitor cell-like cell bank.

Specifically, in the step S1, the obtained first hepatic progenitor cell-like cell line, the second hepatic progenitor cell-like cell line, the third hepatic progenitor cell-like cell line, the fourth hepatic progenitor cell-like cell line, the fifth hepatic progenitor cell-like cell line, and the sixth hepatic progenitor cell-like cell line are respectively subjected to the cryopreservation treatment to obtain the heterogeneous hepatic progenitor cell-like cell bank.

The hepatic progenitor cell-like cell bank is composed of the first immortal hepatic progenitor cell-like cell line, the second immortal hepatic progenitor cell-like cell line, the third immortal hepatic progenitor cell-like cell line, the fourth immortal hepatic progenitor cell-like cell line, the fifth immortal hepatic progenitor cell-like cell line and the sixth immortal hepatic progenitor cell-like cell line.

The in vitro three-dimensional hepatocyte model is constructed by using the hepatic progenitor cell-like cell bank. The method for constructing the in vitro three-dimensional hepatocyte model is stated in the "Expansion and Differentiation of Human Hepatocyte-derived Liver Progenitor-like Cells and Their Use for the Study of Hepatotropic Pathogens" published in Volume 29, Issue 1, 2018, Cell Research, and is not repeated here. In the process of constructing the in vitro three-dimensional hepatocyte model, a first hepatocyte model line, a second hepatocyte model line, a third hepatocyte model line, a fourth hepatocyte model line, a fifth hepatocyte model line and a sixth hepatocyte model line are obtained by the first immortal hepatic progenitor cell-like cell line, the second immortal hepatic progenitor cell-like cell line, the third immortal hepatic progenitor cell-like cell line, the fourth immortal hepatic progenitor cell-like cell line, the fifth immortal hepatic progenitor cell-like cell line and the sixth immortal hepatic progenitor cell-like cell line, respectively.

In the embodiment of the present invention, the morphology of the first human primary hepatocyte culture and the obtained first hepatic progenitor cell-like cell line after transformation-cultured are observed under a cell inverted microscope at a magnification of 40 times. A morphological schematic diagram of human primary hepatocytes as shown in FIG. 1 and a schematic diagram of the structure of the first hepatic progenitor cell-like cell line as shown in FIG. 2 are obtained.

Figure 2:
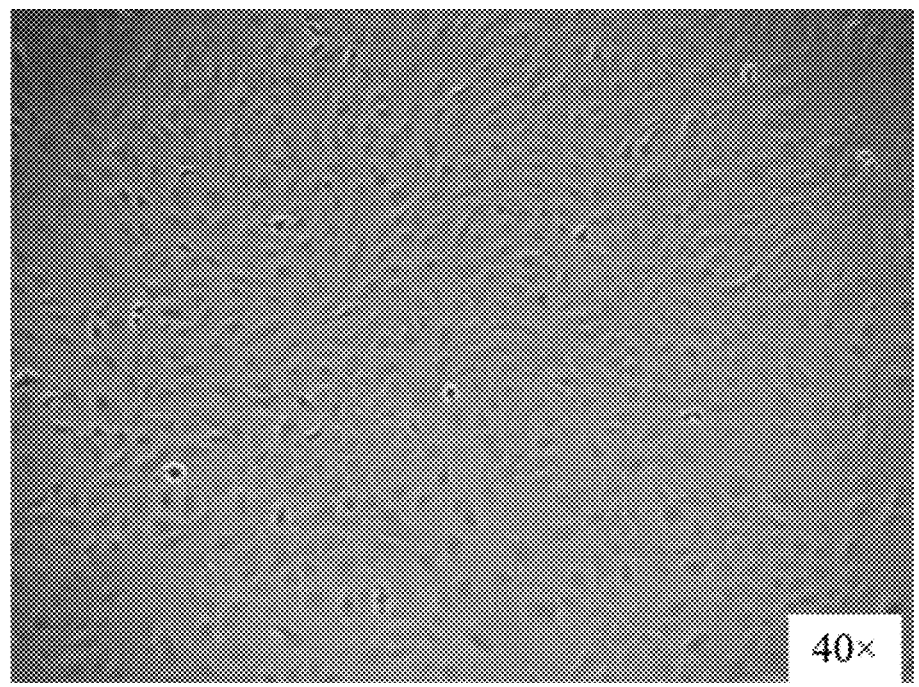
FIG. 2 is a schematic diagram of the morphology of a first hepatic progenitor cell-like cell line of the present invention.

Referring to FIGS. 1 and 2, after the transformation culture, the human primary hepatocytes in the first human primary hepatocyte culture are gradually transformed into the first hepatic progenitor cell-like cell line with a more regular morphology, which is conducive to obtain a more stable proliferation ability.

Figure 3:
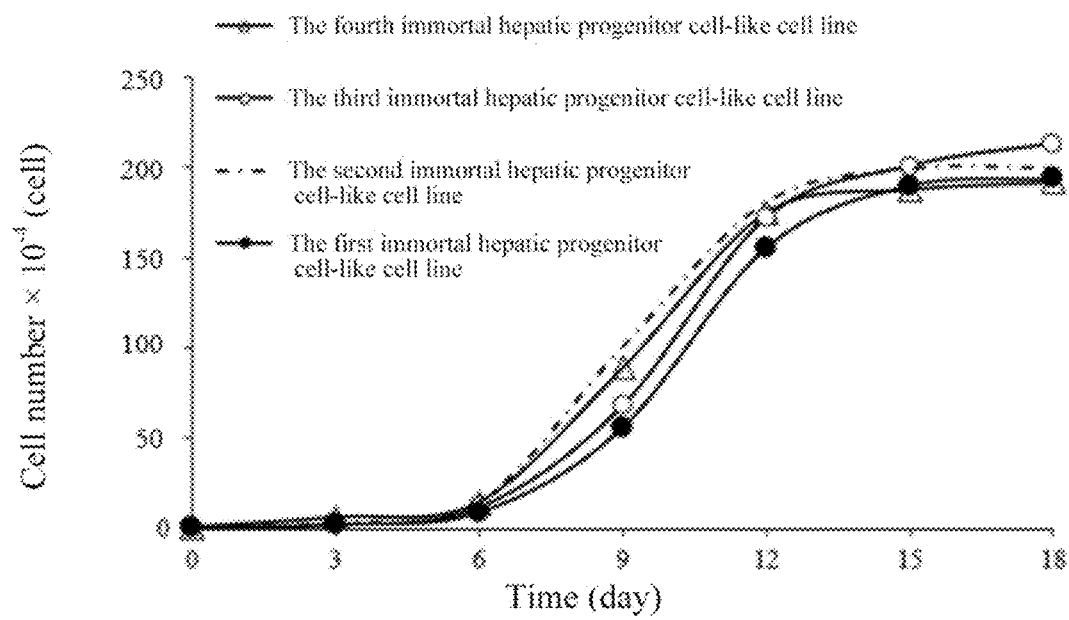
FIG. 3 is a comparison diagram of the proliferation performance of a first immortal hepatic progenitor cell-like cell line, a second immortal hepatic progenitor cell-like cell line, a third immortal hepatic progenitor cell-like cell line and a fourth immortal hepatic progenitor cell-like cell line of the present invention.
Figure 4A:
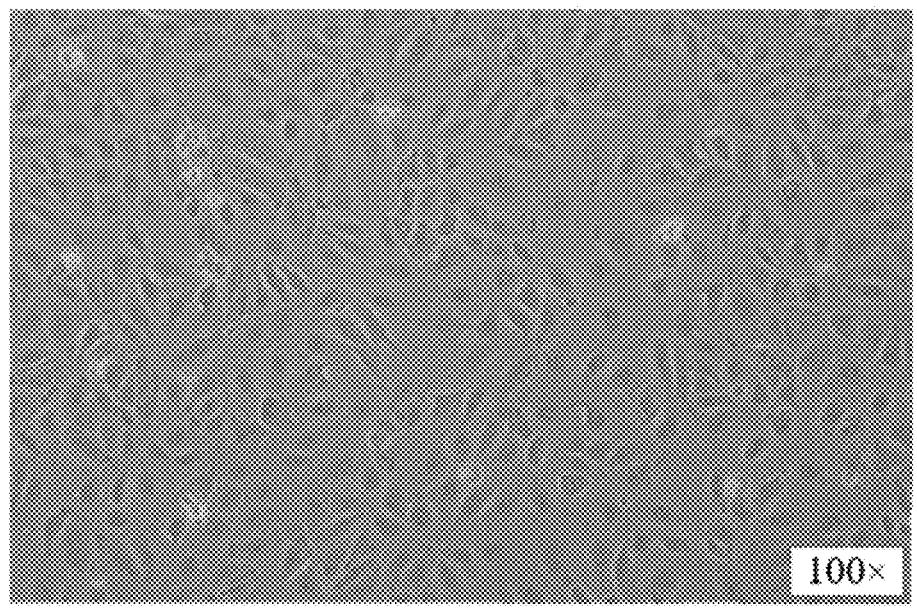
FIG. 4a is a schematic diagram of the morphology of the first immortal hepatic progenitor cell-like cell line after in vitro proliferation-culture of the present invention.
Figure 4B:
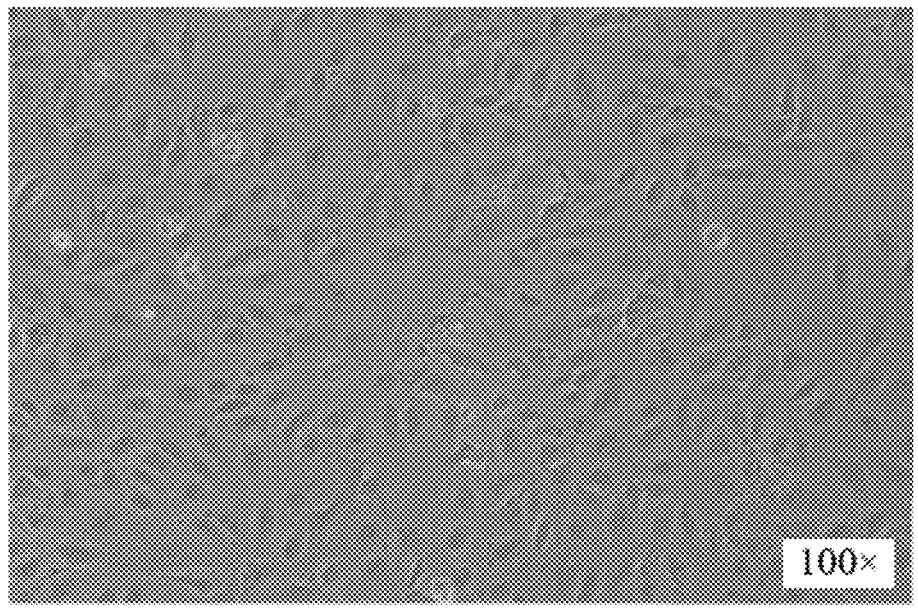
FIG. 4b is a schematic diagram of the morphology of the second immortal hepatic progenitor cell-like cell line after in vitro proliferation-culture of the present invention.
Figure 4C:
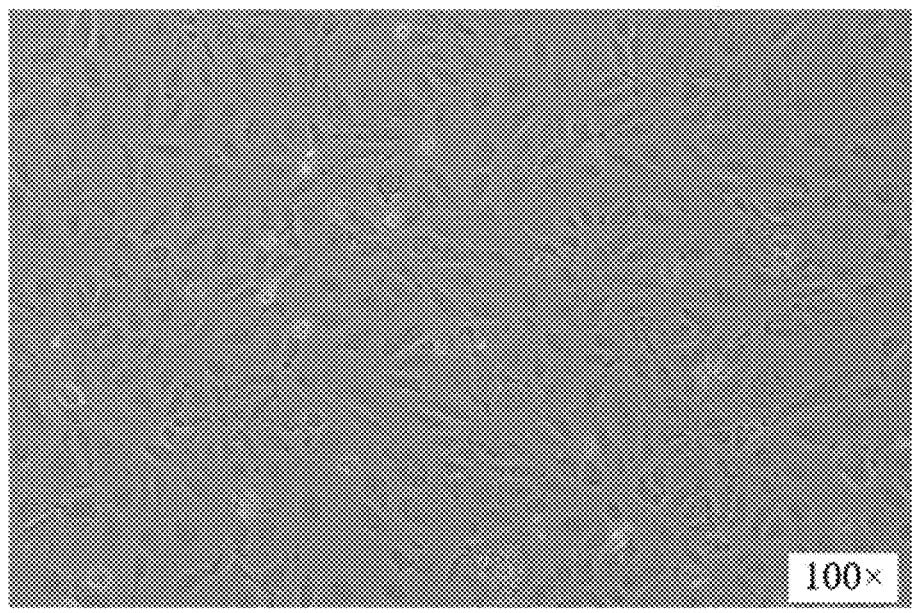
FIG. 4c is a schematic diagram of the morphology of the third immortal hepatic progenitor cell-like cell line after in vitro proliferation-culture of the present invention.
Figure 4D:
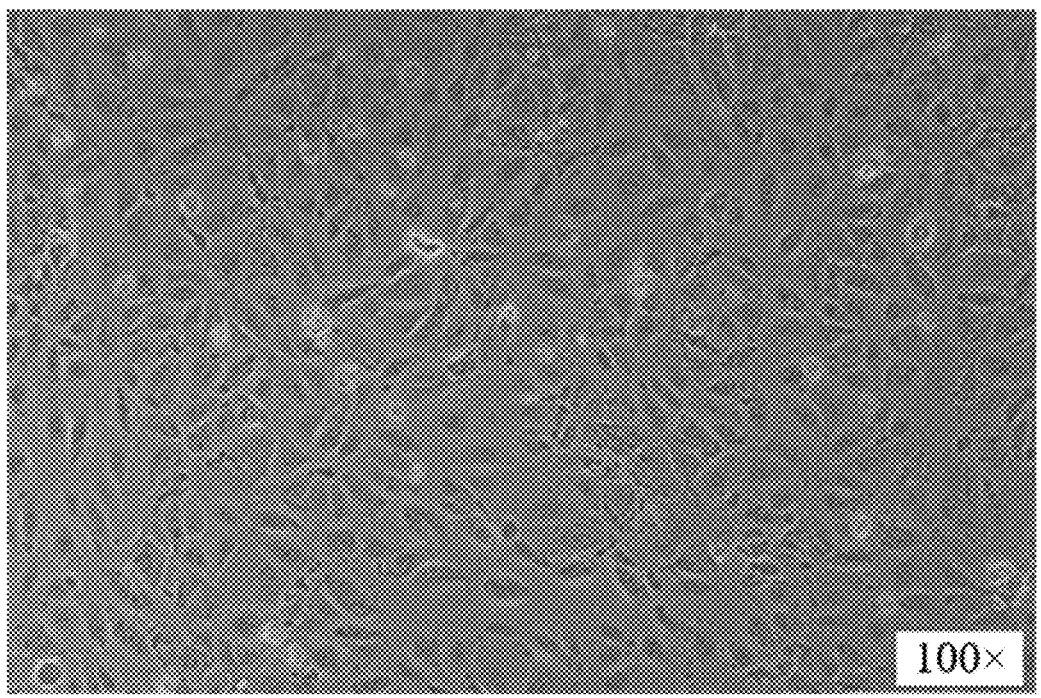
FIG. 4d is a schematic diagram of the morphology of the fourth immortal hepatic progenitor cell-like cell line after in vitro proliferation-culture of the present invention.

In the embodiment of the present invention, the first immortal hepatic progenitor cell-like cell line, the second immortal hepatic progenitor cell-like cell line, the third immortal hepatic progenitor cell-like cell line, and the fourth immortal hepatic progenitor cell-like cell line are in vitro proliferation-cultured for 40 passages, 30 passages, 20 passages, and 10 passages, respectively, to obtain a comparison chart of proliferation performance as shown in FIG. 3, and the corresponding doubling times are also counted.

The specific implementation of the in vitro proliferation-culture and the standard method of proliferation performance and doubling time is stated in the "Expansion and Differentiation of Human Hepatocyte-derived Liver Progenitor-like Cells and Their Use for the Study of Hepatotropic Pathogens" published in Volume 29, Issue 1, 2018, Cell Research, and will not be repeated here.

Referring to FIG. 3, in the 20 days period of in vitro proliferation-culture, the cell number and the proliferation rate of the first immortal hepatic progenitor cell-like cell line, the second immortal hepatic progenitor cell-like cell line, the third immortal hepatic progenitor cell-like cell line, and the fourth immortal hepatic progenitor cell-like cell line are not much different, while the corresponding doubling times of the first immortal hepatic progenitor cell-like cell line, the second immortal hepatic progenitor cell-like cell line, the third immortal hepatic progenitor cell-like cell line and the fourth immortal hepatic progenitor cell-like cell line are $29.65\pm0.4$ hours, $28.32\pm0.1$ hours, $30.90\pm0.3$ hours and $28.92\pm0.1$ hours, respectively. It can be seen that the human primary hepatocyte cultures obtained from the different donor sources in Embodiments 1-4 after the transformation-culture and the following cryopreservation treatment can be successfully established for immortalization and provided with good in vitro proliferation ability.

In the embodiment of the present invention, the morphology of the first immortal hepatic progenitor cell-like cell line, the second immortal hepatic progenitor cell-like cell line, the third immortal hepatic progenitor cell-like cell line and the fourth immortal hepatic progenitor cell-like cell line are observed under a cell inverted microscope at a magnification of 100 times, and the corresponding morphological schematic diagrams as shown in FIGS. 4a to 4d are obtained.

Referring to FIGS. 4a to 4d, the first immortal hepatic progenitor cell-like cell line, the second immortal hepatic progenitor cell-like cell line, the third immortal hepatic progenitor cell-like cell line and the fourth immortal hepatic progenitor cell-like cell line have similar morphologies, and the growth characteristics thereof are basically not affected.

Figure 5:
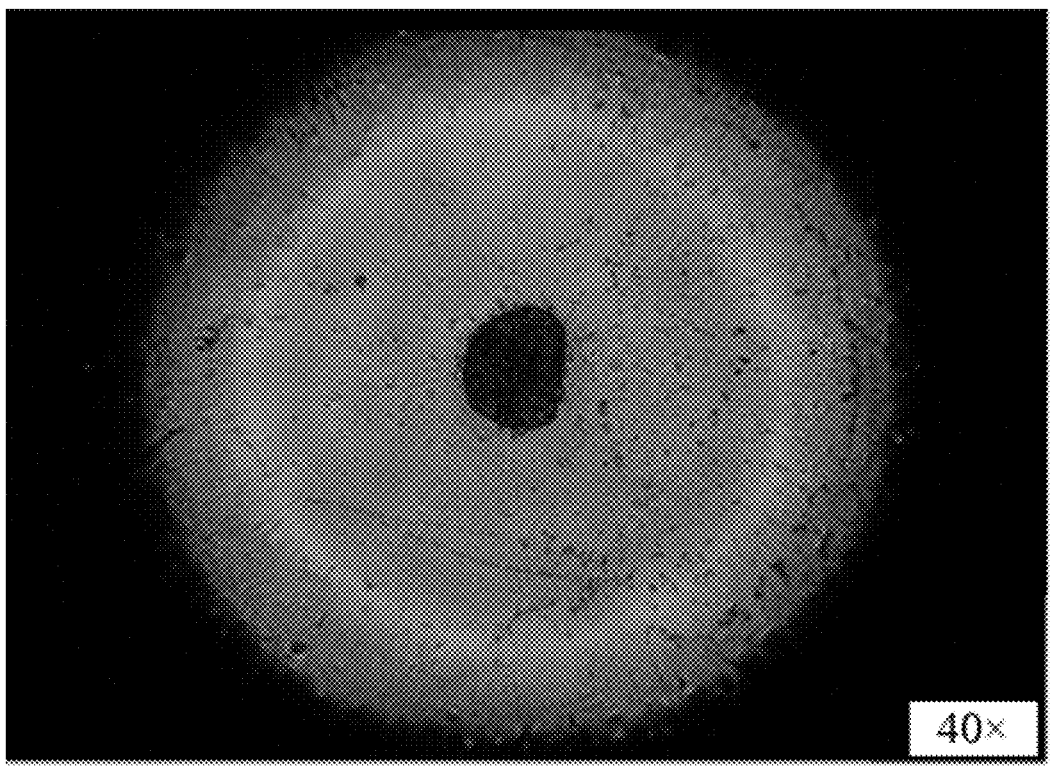
FIG. 5 is a schematic diagram of the morphology of a first hepatocyte model line of the present invention.
Figure 6A:
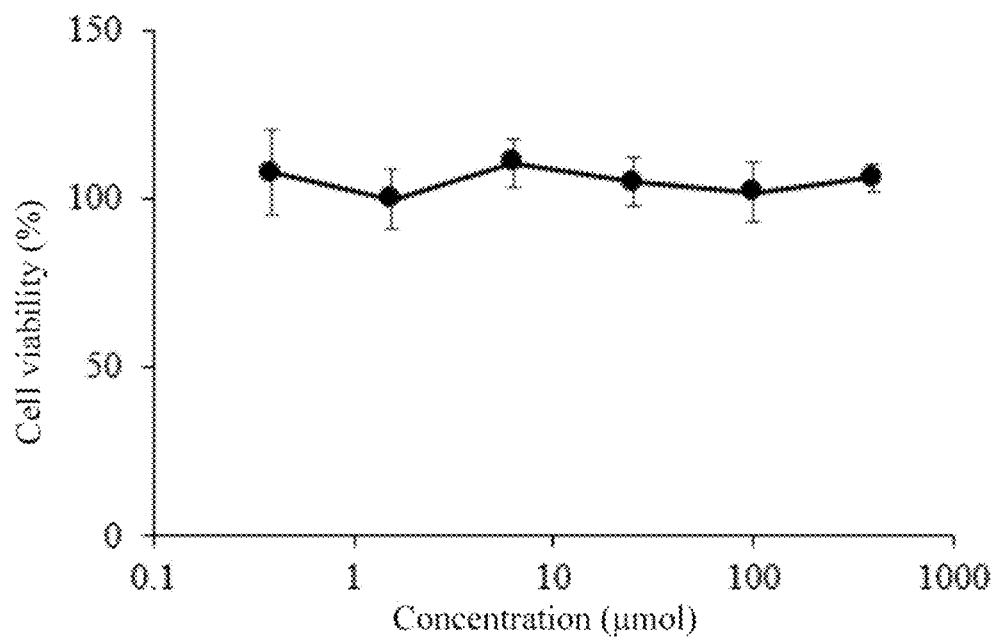
FIG. 6a is a schematic diagram of the specific hepatotoxicity of Erlotinib in the first hepatocyte model line of the present invention.
Figure 6B:
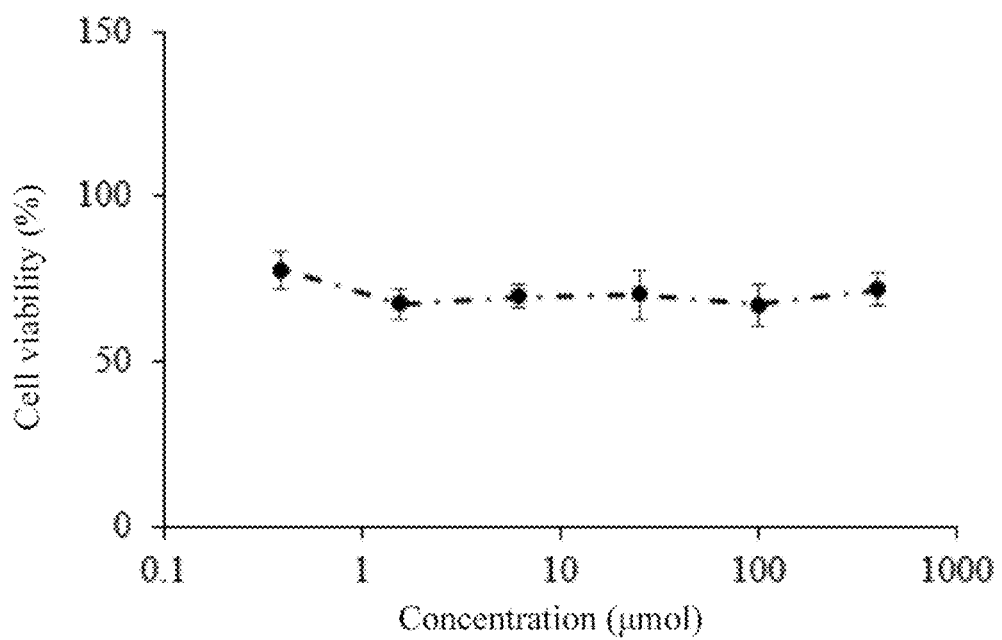
FIG. 6b is a schematic diagram of the specific hepatotoxicity of Erlotinib in the second hepatocyte model line of the present invention.
Figure 6C:
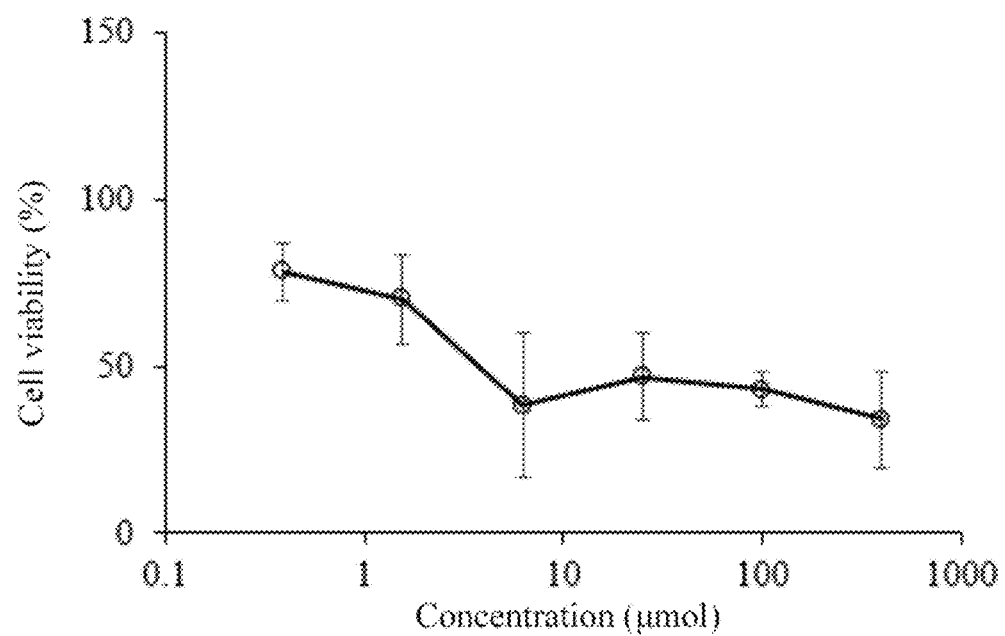
FIG. 6c is a schematic diagram of the specific hepatotoxicity of Erlotinib in the third hepatocyte model line of the present invention.
Figure 6D:
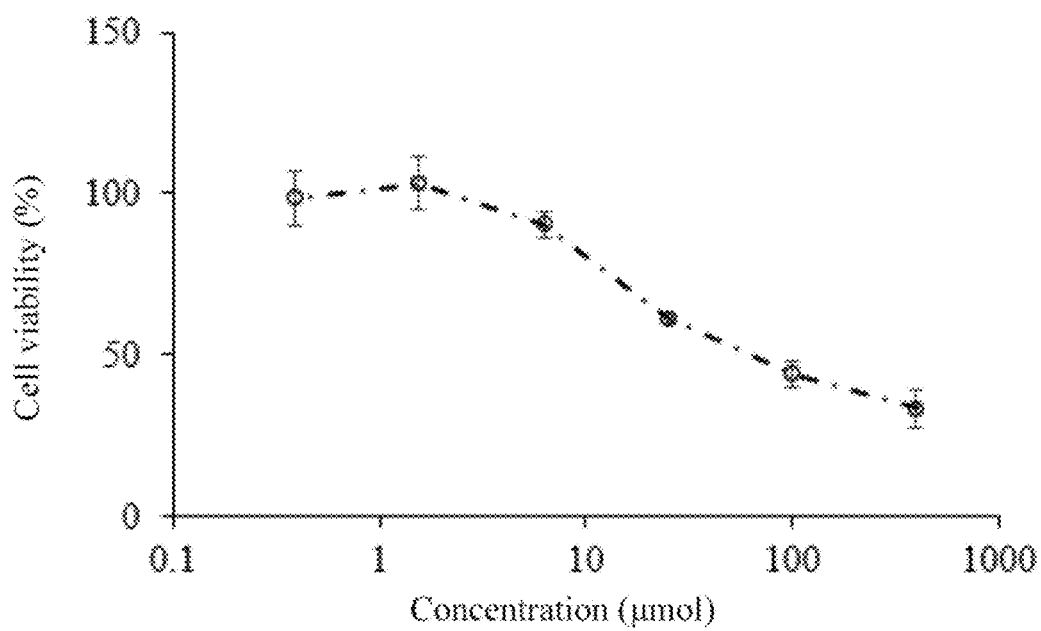
FIG. 6d is a schematic diagram of the specific hepatotoxicity of Erlotinib in the fourth hepatocyte model line of the present invention.
Figure 6E:
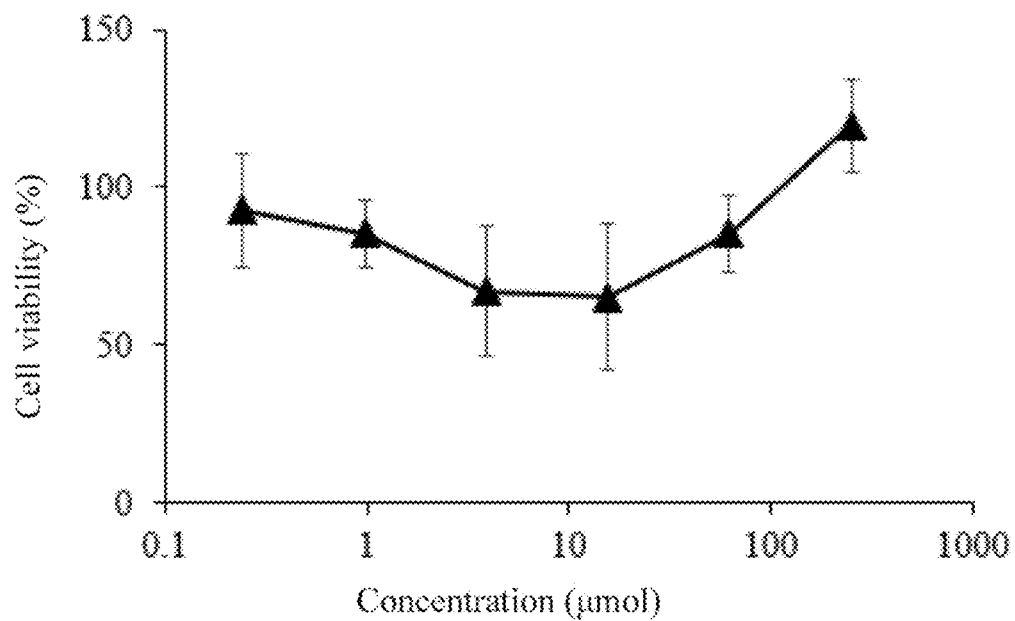
FIG. 6e is a schematic diagram of the specific hepatotoxicity of Erlotinib in the fifth hepatocyte model line of the present invention.
Figure 6F:
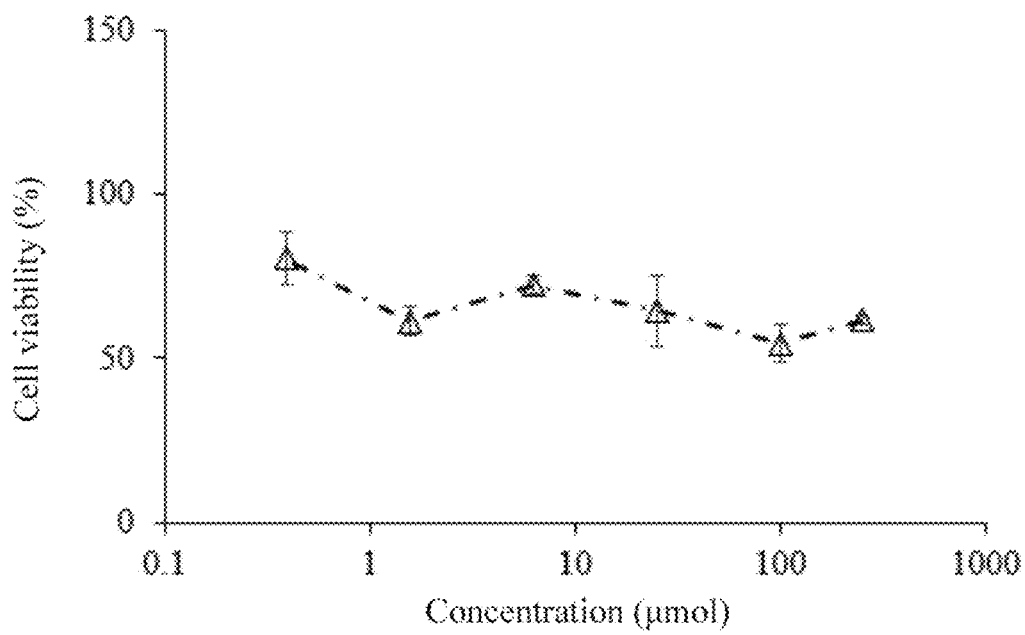
FIG. 6f is a schematic diagram of the specific hepatotoxicity of Erlotinib in the sixth hepatocyte model line of the present invention.

In the embodiment of the present invention, the morphology of the first hepatocyte model line in the in vitro three-dimensional hepatocyte model is observed under a cell inverted microscope at a magnification of 100 times, and the morphological schematic diagram as shown in FIG. 5 is obtained.

Referring to FIG. 5, the first hepatocyte model line has a relatively regular spherical structure, indicating good hepatocyte function.

In the embodiment of the present invention, the specific toxic drug Erlotinib is used to characterize the specific hepatotoxicity of the in vitro three-dimensional hepatocyte model.

The specific method for characterizing hepatotoxicity is:

Preparing a Erlotinib solutions with concentrations of 250 μMol/L, 62.5 μMol/L, 15.625 μMol/L, 3.9 μMol/L, 0.97 μMol/L, 0.24 μMol/L by dimethyl sulfoxide (DMSO), and using DMSO as a blank reference.

Each hepatocyte model line in the in vitro three-dimensional hepatocyte model is co-cultured with different concentrations of Erlotinib aqueous solution for 48 hours.

After the co-culture is completed, the PrestoBlue™ cell viability testing reagent produced by Life Technologies is used to characterize the Erlotinib-specific hepatotoxicity in each culture obtained after the co-culture, respectively. The specific methods for the co-culture and the characterization of the Erlotinib-specific hepatotoxicity are common methods known by those skilled in the art and will not be repeated here.

FIGS. 6a to 6f are the schematic diagrams of Erlotinib-specific hepatotoxicity of the first hepatocyte model line, the second hepatocyte model line, the third hepatocyte model line, the fourth hepatocyte line strain, the fifth hepatocyte line and the sixth hepatocyte model line, respectively.

Referring to FIGS. 6a to 6f, although the cell viability of the first hepatocyte model line, the second hepatocyte model line, the fifth hepatocyte model line, and the sixth hepatocyte model line basically does not significant changed and the specific hepatotoxicity to Erlotinib does not shown with the increase in the concentration of Erlotinib solution, the cell viability of the third hepatocyte model line and the fourth hepatocyte model line basically have a significant downward trend with the increase in the concentration of Erlotinib solution, which shows the benefits to facilitate the research on the Erlotinib-specific hepatotoxicity in addition to the Erlotinib-specific toxicity.

Embodiment 8

The Embodiment 8 of the present invention also provides the application of the immortal hepatic progenitor cell-like cell line in bioartificial liver.

Specifically, the immortal hepatic progenitor cell-like cell line with the preservation number of CCTCC NO: C2019125 is used for the application. The application includes: cell proliferation, construction of animal models, establishment of extracorporeal circulation system, and sampling with testing.

The cell proliferation includes: loading the immortal hepatic progenitor cell-like cell line with the preservation number of CCTCC NO: C2019125 on a carrier, and then culturing the cell through a liquid-gas interactive bioreactor to achieve hepatocyte proliferation.

Figure 7:
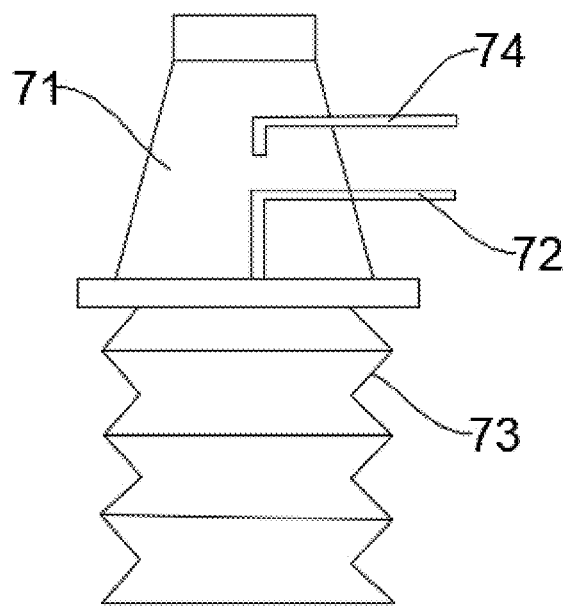
FIG. 7 is a schematic structural diagram of a liquid-gas interactive bioreactor of the present invention.

FIG. 7 is a schematic structural diagram of a liquid-gas interactive bioreactor of the embodiment of the present invention.

Referring to FIG. 7, the liquid-gas interactive bioreactor 7 has a container body 71 and a bellows 73 that communicate with each other inside, and a liquid outlet tube 72 and a liquid inlet tube 74 disposed on the container body 71. The immortal hepatic progenitor cell line with the preservation number of CCTCC NO: C2019125 is loaded on a blank slide to form a load slide, and then is placed on the container body 71. The culture solution used in the contents stated in pages 8 to 22, Volume 29, Issue 1, 2019, Cell Research is introduced into the bellows 73 through the liquid inlet tube 74. The bellows 73 is driven to lift up and down in order to make the load slide periodically to be immersed in the cell culture medium for liquid phase material exchange. The load slide is able to perform gas phase material exchange with oxygen in the air within the container body 71 to perform the cell proliferation. The mass of the blank slide is 11 grams.

Specifically, the rate of the lifting movement of the bellows 73 is controlled to be 0.5-5 mm/s, and the time for the load slide to perform the liquid phase material exchange in each lifting cycle of the bellows 73 is 100-300 seconds, the time to perform the gas phase material exchange is 5-120 seconds. The time of the liquid phase material exchange refers to the time that the load slide is immersed in the cell culture medium, and the time of the gas phase material exchange refers to the time that the load slide is exposed to the air. The period of the cell proliferation is 14 days.

During the cell proliferation, the cell culture medium is replaced every 24 hours to facilitate effective three-dimensional expansion of cells.

Figure 8:
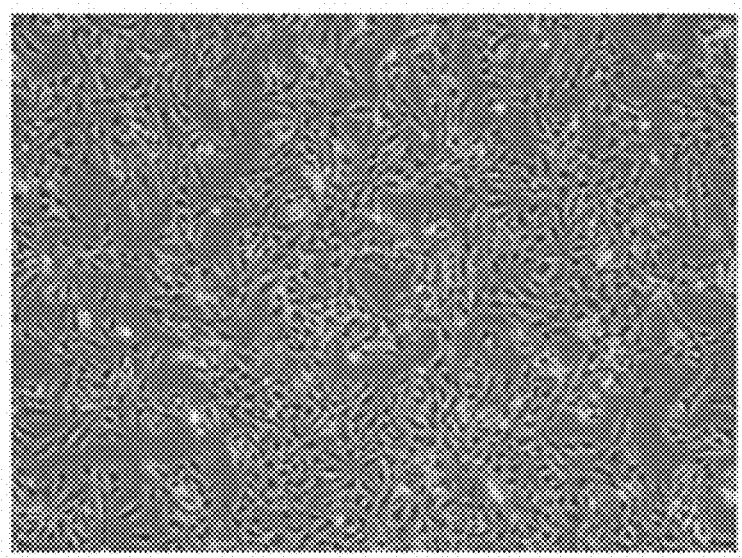
FIG. 8 is a schematic diagram of the morphology of the proliferated cells obtained after cell proliferation of the present invention, which is observed under a cell inverted microscope at a magnification of 100 times.

After 14 days of the cell proliferation, the number of hepatocytes loaded on the slide is expanded from $0.5 \times 10^9$ cells before culture to $2.5 \times 10^9$ cells. The proliferated cells obtained after the cell proliferation is observed under an inverted microscope at a magnification of 100 times to obtain the morphological schematic diagram shown in FIG. 8. Referring to FIG. 8, it can be seen that the obtained proliferated cells have a relatively regular morphological structure, which is conducive to exerting good cell functions.

Embodiment 8 of the present invention studies the gene expression levels of different functional genes of the proliferated cells obtained at different proliferation times, in order to investigate cell functions.

Specifically, the RNAfast200 kit with the article number of 220010 produced by Shanghai Fastagen Biotechnology Co., Ltd. is used to extract the RNA of the proliferated cells, and then the reverse transcriptase with the article number of 18064014 produced by Invitrogen is used to reverse transcript the obtained RNA to cDNA respectively. Finally, the relevant functional genes are finally expressed respectively by fluorescent quantitative PCR. The specific expressing method of the fluorescent quantitative PCR is known by those skilled in the art and will not be repeated herein.

Related functional genes are carbamoyl phosphate synthetase 1 (CPS1), α1-antitrypsin (Alpha-1-antitrypsin, AAT), albumin (Alb), drug metabolism enzyme CYP3A4, protein coding gene GSTA2 and multidrug resistance related protein MRP4. Please refer to Table 1 for the average gene expression levels of CPS1, AAT, Alb, CYP3A4, GSTA2 and MRP4 of the proliferated cells obtained after 2 days of the cell proliferation and the proliferated cells obtained after 14 days of the cell proliferation.

TABLE 1

| Functional Gene | CPS1 | AAT | Alb | CYP3A4 | GSTA2 | MRP4 |
| --- | --- | --- | --- | --- | --- | --- |
| Day 2 | 1 | 1 | 1 | 1 | 1 | 1 |
| Day 14 | 5 | 2 | 6 | 4 | 10 | 1.5 |

It can be seen from Table 1 that after 14 days of the cell proliferation, the average gene expression levels of CPS1, AAT, Alb, and GSTA2 all increased significantly, and the proliferated cells shows good protein synthesis functions; the significant increase of GSTA2 and MRP4 in average gene expression levels indicates that proliferated cells have good drug metabolism capabilities.

The construction of the animal model includes: dissolving D-(+)-Galactosamine hydrochloride (D-gal) in an aqueous glucose solution with a mass concentration of 5%, diluting to 0.5 g/mL and then adjusting the pH value to 6.8 by using sodium hydroxide aqueous solution of 1 mol/L to form a D-gal solution; filtering and sterilizing the D-gal solution by using a syringe filter with an average pore size of 0.22 microns.

Six-year-old, 20-30 kg weight of healthy experimental piglets are fasted for 8 hours before general anesthesia, and drinking water is forbidden for 4 hours before general anesthesia; after general anesthesia, Sedinger puncture technique under ultrasound guidance is performed to puncture the piglet's femoral vein and external jugular vein; after the spontaneous breathing of piglet is recovered, the D-gal solution is injected into the body of the spontaneous breathing recovered piglet by bolus injection at a dose of 0.5 g per kilogram of piglet. The bolus injection is completed within 30 minutes to construct a biological model of acute hepatic failure.

Whole blood is taken for testing. When the testing results show that the alanine aminotransferase (ALT) and aspartate aminotransferase (AST) of the experimental piglets are higher than 200 U/L and 1000 U/L, respectively, the international normalized ratio (INR) reaches 2-3, and the blood ammonia value is higher than 45 μmon, it is judged that the biological model of acute hepatic failure is constructed successfully.

Figure 9:
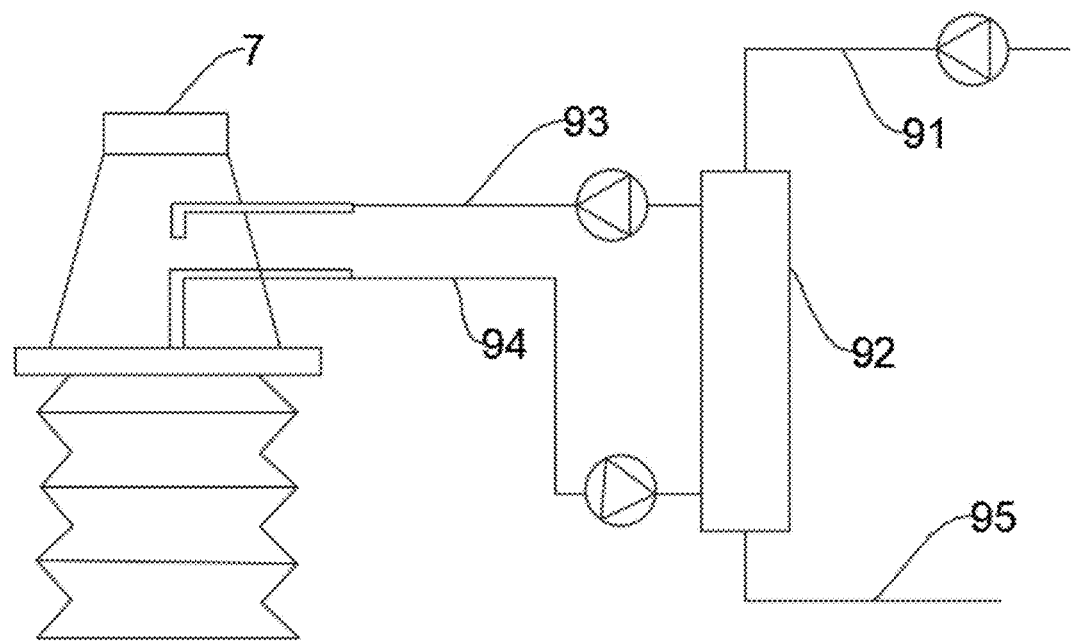
FIG. 9 is a schematic diagram of the structure of an extracorporeal circulation system of the present invention.

FIG. 9 is a schematic diagram of the structure of an extracorporeal circulation system of Embodiment 8 of the present invention.

Referring to FIG. 9, the establishment of the extracorporeal circulation system includes:

After the biological model of acute hepatic failure is successfully constructed, the blood of the experimental piglet is connected to a first catheter 91 through the femoral venous puncture catheter and is pumped to a plasma separator 92. Simultaneously, heparin is added into the plasma separator 92 through the first catheter 91. The heparin dose of whole body is controlled to 100 units per kilogram of piglets.

The separated plasma is pumped into the liquid-gas interactive bioreactor 7 by the plasma separator 92 through a second catheter 93. The obtained slide after the cell proliferation is placed in the liquid-gas interactive bioreactor 7, then the liquid-phase material exchange and the gas-phase material exchange between the plasma and the slide are controlled by the liquid-gas interactive bioreactor 7. Specifically, referring to FIG. 7, the rate of the lifting movement of the bellows 73 is controlled to be 2 mm/s, the time for the load slide to perform the liquid phase material exchange in each lifting cycle of the bellows 73 is 120 seconds, and the time to perform the gas phase material exchange is 10 seconds. The specific control method will not be repeated here, please refer to the description of the cell proliferation.

The obtained detoxified plasma is pumped into the plasma separator 92 through a third catheter 94 to be remixed with blood cells to form purified blood and is returned into the experimental piglets through a fourth catheter 95 to complete the cycle treatment. The total period of the cycle treatment is 3 h.

The experimental piglets are continually raised after the cycle treatment. The experimental piglets can stand stably and gradually resume their diet for 65 hours after the cycle treatment is completed and can still survive for 96 hours later.

The sampling with testing includes: taking blood from the experimental piglets at different times within 72 hours after the cycle treatment is completed, and inspecting serum biochemical indexes and hepatic blood coagulation ability indexes.

In addition, the embodiment of the present invention provides Comparative Example 1. After the blood of the experimental piglets is filtered through a bilirubin adsorption column of model BS330 and a hollow fiber tube, it flows through the blank liquid-gas interactive bioreactor 7 through the extracorporeal circulation system shown in FIG. 7 to perform 3 hours of cycle treatment. The slide, which is blank, in the liquid-gas interactive bioreactor 7 is a blank slide. Please refer to the foregoing content about the rest of the specific control process.

Among them, the serum biochemical indexes of Embodiment 8 and Comparative Example 1 are ALT content, AST content, serum ammonia content, total bilirubin (TBiL) content, lactate dehydrogenase (LDH) content and Alb content. Please refer to Table 2 for specific values.

TABLE 2

| Testing time | 0 hour | | 72 hours | |
| --- | --- | --- | --- | --- |
| | Embodiment 8 | Comparative Example 1 | Embodiment 8 | Comparative Example 1 |
| ALT | 66 | 39 | 177 | 688 |
| AST | 23 | 30 | 150 | 2187 |
| Ammonia | 16.88 | 19.38 | 8.27 | 436 |
| TBiL | 0.7 | 1.0 | 2.6 | 56.7 |
| LDH | 458 | 326 | 1005 | 5744 |
| Alb | 40.9 | 39.4 | 39.4 | 29.0 |

In Table 2, the unit of ALT and AST is U/L, the unit of Ammonia, TBiL and LDH is μmon, and the unit of Alb is g/L.

Referring to Table 2, the ALT of Comparative Example 1 and Embodiment 8 increased at the same time as the AST increased in 72 hours after the cycle treatment is completed, but the increase level of ALT and AST of Embodiment 8 is lower than the increase level of the corresponding serum biochemical indexes of Comparative Example 1. The serum ammonia content of Comparative Example 1 and Embodiment 8 are both increased, but the increase level of serum ammonia content of Embodiment 8 is also lower than the increase level of the corresponding serum biochemical indexes of Comparative Example 1.

Further, according to the data measured at different times within 72 hours after the cycle treatment is completed, the ALT of Comparative Example 1 is sharply increased from 200 U/L to 2500 U/L within 24 hours after the cycle treatment is completed, and then is sharply dropped to 700 U/L; while the ALT of Embodiment 8 is always kept within 200 U/L, and a slow downward trend is shown within 48 to 72 hours after the cycle treatment is completed.

The ammonia of Comparative Example 1 and Embodiment 8 is increased to 80 μmon and 50 μmon, respectively within 24 hours after the cycle treatment is completed. Then, the ammonia of Embodiment 8 is continued to decrease until the value not higher than 10 μmol/L, and the ammonia of Comparative Example 1 is significantly increased to 450 μmol/L after 24 hours of slow decrease.

Based on the data of ALT, AST and Ammonia, it can be seen that the proliferated cells formed by the proliferation of the immortal hepatic progenitor cell-like cell line of Embodiment 8 have a certain detoxification ability and can effectively reduce the level of hepatic injury compared to Comparative Example 1.

Referring to Table 2, for Embodiment 8, TBiL is increased within 72 hours after the cycle treatment is completed, but the increase amplitude is not large, while the TBiL of Comparative Example 1 is increased significantly.

Further, according to the data measured at different times within 72 hours after the cycle treatment is completed, the TBiL of Comparative Example 1 is significantly increased to 60 μmol/L within 48 hours after the cycle treatment is finished, and then is dropped to 56.7 μmol/L. The TBiL of Embodiment 8 never exceeded 3.5 μmol/L.

According to the data of TBiL, it can be seen that after detoxification of the proliferated cells formed by the proliferation of the immortal hepatic progenitor cell-like cell line in Embodiment 8, the experimental piglets of Embodiment 8 show better hepatic secretion and excretion functions than those of Comparative Example 1.

Referring to Table 2, 72 hours after the cycle treatment is completed, the decrease amplitude of Alb of Embodiment 8 is very low. According to the data measured at different times within 72 hours after the cycle treatment is completed, the Alb of Embodiment 8 varies between 36-40 g/L.

Referring to Table 2, 72 hours after the cycle treatment is completed, the decrease amplitude of Alb of Comparative Example 1 is higher than that of Embodiment 8. According to the data measured at different times within 72 hours after the cycle treatment is completed, the Alb of Comparative Example 1 varies between 29-35 g/L.

According to the data of Alb, it can be seen that after detoxification of the proliferated cells formed by the proliferation of the immortal hepatic progenitor cell-like cell line in Embodiment 8, the experimental piglets of Embodiment 8 show better hepatic synthesize and protein storage ability than those of Comparative Example 1.

Referring to Table 2, 72 hours after the cycle treatment is completed, the LDH of Comparative Example 1 is much higher than that of Embodiment 8, which shows abnormal activity. According to the data measured at different times within 72 hours after the cycle treatment is completed, the LDH of Comparative Example 1 has maintained a significant upward trend since the cycle treatment is completed. Although the LDH of Embodiment 8 also has an upward trend, the increase amplitude is much lower than that of Comparative Example 1.

According to the data of LDH, it can be seen that the liver of the experimental piglets of Comparative Example 1 has more severe hepatic injury than the liver of the experimental piglets of Embodiment 8.

The hepatic blood coagulation ability indexes include prothrombin time (PT), thrombin time (TT), activated partial thromboplastin time (APTT), and INR. The specific testing means are conventional technical means known by those skilled in the art and will not be repeated here.

Specifically, the PT of Comparative Example 1 significantly increased from 20 seconds to 150 seconds from the 24$^{th}$ hour to the 72$^{nd}$ hour after the cyclic treatment is completed, while the PT of Embodiment 8 never exceeded 30 seconds. Further, from the 24$^{th}$ to the 72$^{nd}$ hour after the cyclic treatment is completed, PT has a slow downward trend, and is finally dropped to 12 seconds.

The INR of Comparative Example 1 is increased significantly from 1.78 to 8 from the 24$^{th}$ hour to the 72$^{nd}$ hour after the cycle treatment is completed, while the INR of Embodiment 8 never exceeded 2.6. Further, from the 24$^{th}$ to the 72$^{nd}$ hour after the cyclic treatment is completed, APTT has a slow downward trend, and is finally dropped to 1.05.

The experimental piglets of Comparative Example 1 and the experimental piglets of Embodiment 8 shows little difference in TT measured within 48 hours after the cycle treatment is completed, and both shows an increasing trend, specifically from about 20 seconds to 40 seconds. Around 72 hours after the cycle treatment is completed, the TT of Embodiment 8 is dropped to 21 seconds, while the TT of Comparative Example 1 is continued to rise to about 50 seconds.

The APTT measured by the experimental piglets of Comparative Example 1 and the experimental piglets of Example 8 shows a slow increase trend within 24 hours after the cycle treatment is completed. Specifically, the APTT of Comparative Example 1 is increased to 20 seconds, and the APTT of Embodiment 8 is increased to 28 seconds; within 24 hours to 72 hours after the cycle treatment is completed, the APTT of Comparative Example 1 is significantly increased to 60 seconds, while the APTT of Embodiment 8 has a downward trend, and is finally dropped to 18 seconds.

Based on the above hepatic blood coagulation ability indexes, it can be seen that the liver of the experimental piglets of Comparative Example 1 has a significantly reduced ability to synthesize coagulation factors, and the level of hepatic injury is high.

In summary, the use of the proliferated cells formed by the proliferation of the immortal hepatic progenitor cell-like cell line of Embodiment 8 to detoxify plasma has a positive auxiliary effect on the normalization of the aforementioned serum biochemical indexes and hepatic blood coagulation ability indexes.

In addition, more importantly, after the liquid-gas interactive bioreactor 7 is perfused with the plasma of the experimental piglets, following by the gas phase material exchange and the liquid phase material exchange between the plasma of the experimental piglets and the proliferated cells formed by the proliferation of immortal hepatic progenitor cell-like cell lines, at least one exogenous human growth factor was detected in the purified plasma obtained, thereby proving that the cells formed by the proliferation of the immortal hepatic progenitor cell-like cell line of the embodiments of the present invention applied in bioartificial liver treatment can secrete at least one exogenous human growth factor during the process.

Specifically, the at least one exogenous human growth factor includes any one or more of human hepatocyte growth factor (Human HGF), human transforming growth factor-α (Human TGF-α) and human interleukin-6 (Human IL-6).

Specifically, please refer to Table 3 for the content values of the Human HGF, Human TGF-α, Human IL-6, urea and lactic acid of Embodiment 8 and Comparative Example 1 within 3 hours of the cyclic treatment, which are obtained by sampling and analyzing the plasma of the liquid-gas interactive bioreactor 7 at different times.

TABLE 3

| Time/hour | | 1 | 2 | 3 |
|---|---|---|---|---|
| Human HGF (picogram/mL) | Embodiment 8 | 15.9 | 23.3 | 80.9 |
| | Comparative Example 1 | | 0 | |
| Human TGF-α (picogram/mL) | Embodiment 8 | 7.2 | 7.2 | 8.2 |
| | Comparative Example 1 | | 0 | |
| Human IL-6 (picogram/mL) | Embodiment 8 | 14.7 | 13.1 | 81.9 |
| | Comparative Example 1 | | 0 | |
| Urea (mg/dL) | Embodiment 8 | 50.2 | 59.1 | 78.2 |
| | Comparative Example 1 | 18.2 | 22.4 | 34.3 |
| Lactic acid (mmol/L) | Embodiment 8 | 3.2 | 3.1 | 3.7 |
| | Comparative Example 1 | 5.3 | 5.3 | 5.4 |

Referring to Table 3, in Embodiment 8 of the present invention, the at least one exogenous human growth factor is Human HGF, Human TGF-α, and Human IL-6, which play a positive role in promoting early liver recovery.

In addition, it was detected that the urea level in the purified plasma is increased, which indicates that the cells formed by the proliferation of the immortal hepatic progenitor cell-like cell line in the embodiments of the present invention are helpful in detoxifying the ammonia-based toxic substances in the plasma of the experimental piglets. The decrease in the concentration of lactic acid in the purified plasma further proves that the cells formed by the proliferation of the immortal hepatic progenitor cell-like cell line of the embodiments of the present invention have liver metabolism function.

Embodiment 9

The Embodiment 9 of the present invention provides the application of the immortal hepatic progenitor cell-like cell line in hepatic cell transplantation, which includes the construction of hepatic failure models in mice, and the preparation and transplantation of in vivo bioreactors.

The construction of the acute hepatic failure models in mice includes: providing olive oil containing carbon tetrachloride as an inducer, and subcutaneously injecting 200 microliters of 10% carbon tetrachloride into experimental mice with severe immunodeficiency in NSG. On the next day, a blood sample from the orbital vein is taken as a control; the body weight is recommended to be lost between 1-3 g, and the status is slightly worse than the previous day, so as to complete the construction of the mice models.

The preparation of the in vivo bioreactor includes: preparing cell sphere micro-capsules from the suspension cell clusters formed by a sodium alginate aqueous solution and the proliferated cells prepared from the immortal hepatic progenitor cell-like cell line with the preservation number of CCTCC NO: C2019125 in Embodiment 8, for use in the in vivo bioreactor. The specific preparation method includes: providing a sodium alginate aqueous solution with a mass volume concentration of 1.5% prepared in sterile physiological saline; uniformly mixing the sodium alginate aqueous solution with the suspended cell clusters, so that each milliliter of the obtained mixture contains 3×10$^6$ cells; spraying the mixed solution into a 1.2% calcium chloride aqueous solution for cross-linking for 10 minutes by using an IE-50R packaging machine equipped with a D250 micron sterile nozzle to obtain wet cell sphere micro-capsules; washing the cell sphere micro-capsules with physiological saline to remove free calcium ions, and then washing with deionized water to obtain the cell sphere micro-capsules.

In some embodiments of the present invention, the average diameter of the cell sphere micro-capsules after washing with deionized water does not exceed 500 microns.

Figure 10:
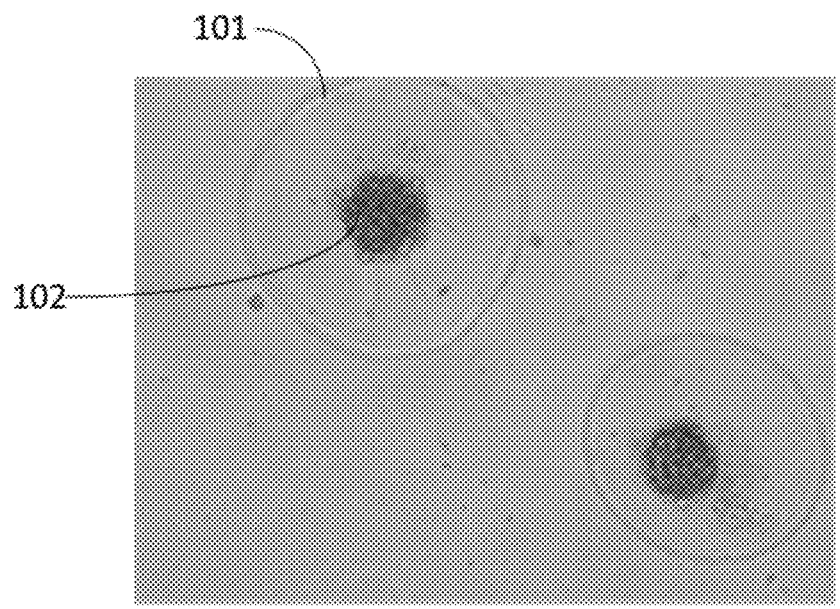
FIG. 10 is an electron micrograph of cell sphere microcapsules of the present invention.

FIG. 10 is an electron micrograph of cell sphere micro-capsules of some embodiments of the present invention. Referring to FIG. 10, since sodium alginate has good biocompatibility and pH sensitivity, it can quickly form a hydrogel under mild conditions, and bind biologically active molecules through salt bondings, hydrogen bondings or hydrophobic interactions. The inside of the cell sphere micro-capsules 101 is coated with the proliferated cell cluster 102, which forms the in vivo bioreactor. The diameter of the in vivo bioreactor is approximately 85 microns.

The transplantation of the in vivo bioreactor includes: redispersing the in vivo bioreactor with physiological saline, and then performing intra-abdominal transplantation to the mice models.

The embodiment of the present invention also provides a Comparative Example 2, which use dispersed microcapsules without proliferated cells to perform intra-abdominal transplantation to the mice models. The difference between the method for preparing microcapsules without proliferated cells and the method for preparing cell sphere micro-capsules is that the suspended cell clusters are not added into the sodium alginate aqueous solution.

Around 7 days after the abdominal cavity transplantation is completed, the surviving experimental mice of Embodiment 9 are euthanized and then dissected for observation. It was found that the in vivo bioreactors are dispersed throughout the abdominal cavity and loosely connected to mesentery and omentum.

After the intra-abdominal transplantation, the Kaplan-Meier method is used to analyze the survival of the experimental mice of Embodiment 9 and Comparative Example 2. The specific analysis method is the conventional technical means known by those skilled in the art and will not be repeated herein.

The result of the survival analysis shows that the survival rate of Embodiment 9 is dropped to 70% on the $2^{nd}$ day after the intra-abdominal transplantation is completed; as the observation time was extended to the $7^{th}$ day after the intra-abdominal transplantation is completed, the survival rate of Embodiment 9 remains unchanged at 70%, and the health status is assessed as semi-dependent; the survival rate of Comparative Example 2 is decreased by 15-20% per day, the survival rate of Comparative Example 2 is decreased to 15% on the $7^{th}$ day after the intra-abdominal transplantation, and the health status is assessed as seriously ill.

The experimental mice of Embodiment 9 and Comparative Example 2 are tested for serum ALT and AST after the intra-abdominal transplantation is completed as well as on the $1^{st}$, $3^{rd}$ and $7^{th}$ day after the intra-abdominal transplantation is completed. The result shows that the serum ALT and AST of Embodiment 9 are both decreased by 70-80% on the $1^{st}$ day after the intra-abdominal transplantation is completed, while the serum ALT and AST of Comparative Example 2 ware both decreased by 30-40%; and the serum ALT and AST of the surviving mice of Embodiment 9 and Comparative Example 2 are both dropped to normal levels on the $3^{rd}$-$7^{th}$ days after the intra-abdominal transplantation is completed.

Based on the above analysis, it can be seen that the proliferated cells prepared by the immortal hepatic progenitor cell-like cell line can facilitate to alleviate the level of hepatic injury in the mice models.

Although the embodiments of the present invention are described in detail above, it is obvious to those skilled in the art that various modifications and changes can be made to these embodiments. However, it should be understood that such modifications and changes fall within the scope and spirit of the present invention described in the claims. Moreover, the present invention described here may have other embodiments, and may be implemented or realized in various ways.

What is claimed is:

1. An immortal hepatic progenitor cell line, wherein the immortal hepatic progenitor cell line has a category name of 81.5 and is preserved in China Center for Type Culture Collection with a preservation number of CCTCC NO: C2019125, the construction method of the immortal hepatic progenitor cell like cell line bank, the construction method comprising:

S1: providing human primary hepatocyte cultures from different donor sources, culturing the human primary hepatocyte culture of each of the donor sources at a seeding density of $0.5 \times 10^4$-$5 \times 10^4$ cells/cm2 for 7-14 days using Transition and Expansion Medium to obtain a hepatic progenitor cell line, and performing cryopreservation treatment to the hepatic progenitor cell like cell line of each of the donor sources obtained after the culture to obtain a heterogeneous hepatic progenitor cell like cell bank;

S2: thawing and proliferating the hepatic progenitor cell like cell line of each of the donor sources to obtain adherent cells of the different donor sources respectively, wherein the confluence rate of the adherent cells of each of the donor sources is 70%-90%;

S3: performing a first subculture treatment and virus infection successively at a seeding density of $2 \times 10^4$-$4 \times 10^4$ cells/cm2 to the adherent cells of each of the donor sources wherein the virus is a lentivirus expressing the HPV E6E7 gene, and replacing a medium during the virus infection, wherein the medium of the culture obtained after the first subculture treatment is replaced at 6-12 hours after adding a Dulbeco's modified Eagle's Medium/12 medium, lentivirus and a polybrene suspension, and then the culture is continually cultured for 24-72 hours to complete the virus infection, a ratio of the number of the lentivirus to the adherent cells is 0.5-60; S4: performing a second subculture treatment at a seeding density of $2 \times 10^4$-$4 \times 10^4$ cells/cm2 for 5-7 days with a passage number of 2 or 3 to the culture of each of the donor sources obtained after the virus infection, and continuously culturing the culture obtained after the second subculture treatment by adding Transition and Expansion Medium as selecting medium to obtain infected cultures of the different donor sources and the medium is replaced every 2-3 days during the second subculture treatment;

S5: continuously subculturing the infected culture of each of the donor sources at a seeding density of $2 \times 10^4$-$4 \times 10^4$ cells/cm2 with a passage ratio of 1:2-1:4 and a passage number of 5-10 to obtain different immortal hepatic progenitor cell lines which will form the immortal hepatic progenitor cell like cell bank.

2. The construction method immortal hepatic progenitor cell line according to claim 1, wherein, in the step S1, the culture is passaged successively for 2 or 3 times and is thereby performed with then the cryopreservation treatment is performed.

3. A method of preparing the hepatic progenitor cell like cell bank according to claim 1, the method comprising:
 constructing an in vitro three-dimensional hepatocyte model;
 and testing a specific hepatotoxicity of a drug by the in vitro three-dimensional hepatocyte model.

* * * * *